United States Patent [19]

Phillips et al.

[11] 4,192,668

[45] Mar. 11, 1980

[54] DESICCANT AND DEFOLIATING SPRAY COMPOSITION FOR LEGUMINOUS PLANTS

[75] Inventors: Clarence A. L. Phillips, Pointe-a-Pierre, Trinidad and Tobago; Henry W. Archer, New York, N.Y.

[73] Assignees: Texaco Trinidad, Inc., Pointe-a-Pierre, Trinidad and Tobago; Texaco Development Corporation, White Plains, N.Y.

[21] Appl. No.: 952,415

[22] Filed: Oct. 18, 1978

Related U.S. Application Data

[63] Continuation-in-part of Ser. No. 835,388, Sep. 21, 1977, abandoned.

[51] Int. Cl.² .............................................. A01N 9/04
[52] U.S. Cl. ............................................ 71/70; 71/127
[58] Field of Search ...................................... 71/70, 127

[56] References Cited

U.S. PATENT DOCUMENTS

| | | | |
|---|---|---|---|
| 2,690,965 | 10/1954 | Emond et al. | 71/127 |
| 2,945,753 | 7/1960 | Brugmann et al. | 71/70 |

*Primary Examiner*—Catherine L. Mills
*Attorney, Agent, or Firm*—Robert A. Kulason; Carl G. Ries; Henry W. Archer

[57] ABSTRACT

Spray oil compositions capable of defoliating and/or desiccating the foliage of leguminous plants so as to facilitate the harvesting thereof are disclosed. The parameter of properties constituent oils must have to provide these effects is given.

4 Claims, No Drawings

DESICCANT AND DEFOLIATING SPRAY COMPOSITION FOR LEGUMINOUS PLANTS

CROSS-REFERENCE TO CO-PENDING APPLICATION

This application is a continuation-in-part of co-pending application Ser. No. 835,388 filed Sept. 21, 1977 and now abandoned.

FIELD OF THE INVENTION

The present invention is generally concerned with the defoliation and/or dessication of legume foliage using mineral spray oils for facilitating mechanical harvesting and is more particularly concerned with petroleum compositions capable of effecting such results.

BACKGROUND OF THE INVENTION

The presence of moisture on the leaves of legumes caused by rainfall, dew of guttation makes combined harvesting of the crop difficult. This problem is particularly serious with Black-eye pea (*Vigna sinensis*). The Black-eye pea plant forms a canopy which remains green and healthy even up to the time the mature yellow and/or dry pods are ready for harvesting. The presence of moisture on the living plant makes mechanical harvesting difficult and crop losses are particularly heavy. Defoliation and/or desiccation of the foliage using mineral spray oils would preclude moisture formation on the leaves thus facilitating mechanical harvesting of the crop.

STATEMENT OF THE PRIOR ART

Defoliation and/or desiccation with chemicals have been in practice for a long period of time on crops such as bean, cotton, corn, sorghum and so on. There is no sharp line of demarcation between defoliants and desiccants, and, in fact, their effects overlap. High application rates of defoliants may give rise to considerable desiccation, while low rates of desiccants may cause a considerable amount of defoliation, especially when used on legumes. Defoliation is accelerated leaf-fall, and requires the functioning of living tissues at the leaf base. Both internal and external factors effect this phenomenon. The principal internal factor is hormones or auxins, the gradient across the leaf base which regulates leaf fall. The main external factors are temperature and moisture. Defoliation is favored by relatively high temperature and moderate leaf moisture. Defoliants appear to act through a mild general injury to both the lamina and petiole. Conversely, desiccation is the chemically accelerated drying of plants or plants parts, and does not require active functioning on the part of the plant. In fact, desiccants are essentially contact herbicides such as herbicidal oils. During desiccation, the role of the plant tissue appears to be completely passive. The tissue contacted by the desiccant rapidly loses moisture and dies. Contigous tissues die somewhat later, but remote tissues remain unaffected. Usually all aerial parts except seeds are killed by the desiccant, and their effects are similar, if not identical, to those of contact herbicides. The degree of injury to some extent determines the rate of desiccation. Environmental factors, especially the relative humidity, are most influential. When the relative humidity is low, desiccation is rapid, and, when high, it is slow.

SUMMARY OF THE INVENTION

In accordance with the invention it has been found that petroleum compositions characterized by a viscosity range at 100° F. of between 34 and 110 SUS, an aromatic content of between 18 and 55 percent, a boiling range of about 180° C. with initial boiling temperature of between 180° and 420° C., a maximum unsulfonated residue of 85 percent, a surface tension of between 24 and 28 dines per centimeter at 30 C and a Harkins spreading coefficient for one minute of between 19 and 28, and for 30 minutes of between about 17 and 31, possess outstanding defoliating and/or desiccating properties for the foliage of leguminous plants. To improve spreading characteristics of the oils, from 0.1 to 1.0 weight percent of a non-ionic surfactants such as Sponto AC 60 may be added. From 56 to 560 liters per hectare of the composition is applied to the foliage of the plants by sprayers.

The preferred petroleum oils tested and shown to have defoliant/desiccant properties when sprayed on Blackeye pea foliage are two gas oils, two lube oil base stocks and two relatively light (low boiling range) oils (Ref. Table I). These spray oils, especially the Heavy Gas Oil, caused moderate to severe desiccation and defoliation when applied to the Black-eye pea foliage. The results of the trials are given in Example I. These oils have the advantage over most chemical compounds used as defoliants and desiccant of being less costly and of not leaving toxic residues on the harvest, plant remains and soil as do chemicals.

The invention is further illustrated in nonlimiting fashion by the following examples.

EXAMPLE I

Three trials (Nos. 14/76, 26/76 & 3/77) were conducted to evaluate the defoliant/desiccant properties of spray oils of varying properties. The Black-eye pea (*Vigna sinesis*) plants used in the trial were grown in plastic pots; 16.5 cm diameter and 17.8 cm deep, containing a growing medium of vermiculite, peatmoss, sand and charcoal mixture. The growing seedlings received Shive's nutrient solution at intervals during their entire period of growth. A randomised block design was used with the treatments replicated three times in three blocks. In Trial Nos. 14/76 and 3/77, the spray oils were applied to the foliage of fruting plants, while in Trial 26/76, the spray oils were applied before the plants commenced fruiting. In Trial No. 14/76, the potted seedlings were taken from the greenhouse and placed in the open 7 days before they were sprayed, while in the other trials, the potted seedlings remained the entire trial period in the greenhouse. The leaf-burn caused by the oils in Trial No. 14/76 tended to be blotchy in appearance due to minimal spreading of the oils on the leaf surfaces. The spreading coefficient of the oils used in Trial Nos. 26/76 and 3/77 were improved by the addition of Sponto AC 60 an oil soluble emulsifier for agricultural spray oils (Ref. Table II). The spray oils were applied with a fixed artist's spray brush at the rate of 5 ml per pot of 3 plants; this rate of application is equivalent to about 560 liters per hectare, and is about 10 times the recommended dosage of Stoddard Solvent used as a herbicide in cotton and soybean. The oils were applied as a blanket spray to the plants. In Trial No. 14/76 the plants were shielded to preclude spray drift, while in Trial Nos. 26/76 and 3/77 the potted plants were placed on a spinning platter (19 revs/minute)

housed in a chamber, and the oils applied from above, 80 cm from the foliage. The extent of leaf-burn and leaf-fall was assessed over a period of about two weeks. The mean data are shown in Tables III to IX.

The lube oil basestocks used are the light and the heavy dewaxed refined waxy distillates (DRWD-5 and DRWD-20) with viscosities of 108.8 and 401 SUS at 100° F. and unsulfonated residues of 83 and 85, respectively. The gas oils had viscosities of 34.5 (EG 9 Gas Oil) and 84.7 (Heavy Gas Oil) SUS at 100° F. respectively and distillation ranges of about 60° C. The viscosity of the Light Cycle Oil was 32.1 SUS at 100° F. The distillation range of White Spirits (Stoddard Solvent) is 28° C. with an IBP of 162° C. The aromatic contents are given for the Light Cycle Oil (59%), EG9 Gas Oil (29.5%) and White Spirits (18.9%). The spreading coefficient of the spray oil is important. The oils' viscosity and ability to spread should be such as to facilitate smooth film formation on the leaf surface. In the first trial (No. 14/76, Tables III and IV), the leaf-burn pattern tended to be blotchy; presumably due to minimal spreading of the oils on the leaf surface. To overcome this tendency, a surfactant, Sponto AC 60, was added to the spray oils at concentrations of 0.05% w/v to 0.2% w/v, thus adjusting the Harkins Spreading Coefficient to a sufficiently high value (Ref. Table II). Lower surfactant concentrations result in lower spreading coefficient while higher concentrations cause the oils to emulsify readily with water. Observations made of the leaf surfaces soon after the oils applied in Trial No. 26/76, Tables V and VI, indicate the presence of a continuous uniform surface film of oil for the oil basestocks, the Light Cycle Oil and the Light Gas Oil. Though the film on the leaf was satisfactory with the Heavy Gas Oil there was the tendency of globular formations possible due to the relatively high viscosity of this oil. The Stoddard Solvent Spray on the other hand tended to have disappeared within a relatively short time due to its relatively low boiling range.

The defoliating and desiccating effects of the oils on the Black-eye pea foliage were manifested within 10 days after the oils were applied unto the leaves. The oils caused moderate to severe leaf-burn and leaf-fall which, for most of the oils, was significant. The Heavy Gas Oil ranked highest having recorded the highest number of leaf-fall in all trial-runs (Table IX). The lube oil basestocks were next in order with DRWD-5 causing slightly higher leaf-fall than DRWD-20. EG9 Gas Oil and Stoddard Solvent were next in rank with the Light Cycle Oil effecting the lowest number of leaf-fall. In Trial No. 14/76, most of the oil sprays caused slight to moderate leaf-burn except that of the Heavy Gas Oil which caused moderate leaf desiccation. In Trials Nos 26/76 and 3/77 (Tables VII and VIII) respectively, the desiccating effect of the oils were moderate to severe in intensity.

TABLE I

PHYSICAL PROPERTIES OF DEFOLIANT/DESICCANT SPRAY OIL[a]

| Sample Description | RS No. /76 | Bromine No. | Spr.Gr. 60/60° F. | Viscosity (SUS at 100° F.) | Aromatics Content By FIA | Unsulfonated Residue % | Distillation °C. IBP | 50% | Dry Point |
|---|---|---|---|---|---|---|---|---|---|
| DRWD* 5 (ex Lube Oil Plant) | 1026 | 1.9 | 0.872 | 108.8 | (b) | 83 | 340 | 418 | 519 |
| DRWD* 20 (ex Lube Oil Plant) | 1025 | 1.5 | 0.898 | 401 | (b) | 85 | 421 | 486 | 577 |
| Light Cycle Oil (ex FCCU) | 1021 | 3.5 | 0.887 | 32.1 | 59 | — | 188 | 241 | 291 |
| Heavy Gas Oil (ex #8 Topping Unit) | 1023 | 3.9 | 0.886 | 84.7 | (b) | 69 | 248 | 356 | 400 |
| EG 9 Gas Oil (ex Tank 65) | 1012 | 1.6 | 0.838 | 34.5 | 29.5 | — | 180 | 259 | 344 |
| White Spirits From Arab. Light ex Tank 40 | 1045 | 0.4 | 0.778 | (c) | 18.9 | — | 162 | 174 | 190 |

[a]Spray oils analysed neat, without surfactant
(b) FIA unsuitable for these samples
(c) Viscosities too low to be expressed as SUS at 100° F.
*Dewaxed refined waxy distillate.

TABLE II

SURFACE ACTIVE PROPERTIES OF DEFOLIANT/DESICCANT CANDIDATE SPRAY OILS

| Sample Description | RS No. /76 | Sponto[a] AC60 Added, % w/v | Surface[b] Tension a 30° C. | Interfacial[b] Tension, 30° C. | | Harkins Spreading Coefficient | |
|---|---|---|---|---|---|---|---|
| | | | | 1 min. | 30 min. | 1 min. | 30 min. |
| DRWD*5 (ex Lube Oil Plant) | 1026 | 0.1 | 27.8 | 5.4 | 3.6 | 19.0 | 21.3 |
| DRWD* 20 (ex Lube Oil Plant) | 1025 | 0.2 | 28.6 | 3.1 | 2.2 | 18.8 | 20.2 |
| Light Cycle Oil (ex FCCU) | 1021 | 0.1 | 26.4 | 9.2 | 7.7 | 15.1 | 17.5 |
| Heavy Gas Oil (ex #8 Topping Unit) | 1023 | 0.1 | 24.0 | 4.5 | 2.7 | 28.2 | 31.0 |
| EG 9 Gas Oil (ex Tank 65) | 1012 | 0.05 | 24.1 | 1.9 | 6.5 | 24.4 | — |
| White Spirits From Arab. Light, ex | 1045 | 0.1 | 24.0 | 5.0 | 3.0 | 30.4 | 33.1 |

TABLE II-continued
SURFACE ACTIVE PROPERTIES OF DEFOLIANT/DESICCANT CANDIDATE SPRAY OILS

| Sample Description | RS No. -/76 | Sponto[a] AC60 Added, % w/v | Surface[b] Tension a 30° C. | Interfacial[b] Tension, 30° C. 1 min. | 30 min. | Harkins Spreading Coefficient 1 min. | 30 min. |
|---|---|---|---|---|---|---|---|
| Tank 46 | | | | | | | |

[a]Sponto AC 60 is an emulsifier made by Witco Chemical Co.
[b]Surface Tension and Interfacial Tension are expressed in dynes/cm.
*Dewaxed refined waxy distillate.

TABLE III
Harvesting Oils: Mean Treatment Effect On The Incidence Of Leaf-Fall Of Black-Eye Pea (Trial #14/76)

| | Treatments | Period after spraying (Days) | | | | | Total | Rank |
|---|---|---|---|---|---|---|---|---|
| | | 1 | 3 | 6 | 8 | 14 | | |
| | | (Leaf-Fall No.) | | | | | | |
| 1 | Heavy Gas Oil (RS-1023/76) | 0.7 | 6.0 | 15.7 | 18.3 | 1.3 | 42.0 a* | 1 |
| 2 | DRWD** 20 (RS-1025/65) | 0.0 | 3.7 | 17.7 | 9.0 | 6.3 | 36.7 ab | 2 |
| 3 | DRWD** 5 (RS-1026/76) | 0.3 | 0.0 | 8.7 | 18.3 | 5.3 | 32.7 abc | 3 |
| 4 | Stoddard Solvent (RS-87/76) | 0.0 | 3.0 | 6.0 | 15.0 | 5.0 | 29.0 abcd | 4 |
| 5 | EG 9 Gas Oil (RS-1012/76) | 1.3 | 1.0 | 9.0 | 11.0 | 4.0 | 26.3 abcd | |
| 6 | Light Cycle Oil (RS-1021/76) | 1.7 | 0.3 | 9.7 | 4.0 | 1.3 | 17.0 bcd | 5 |
| | S.E. ± | | | | | | 7.31 | |
| | C.V. % | | | | | | 56.9 | |

*Figures followed by the same letter are not significantly different (5% level)
**Dewaxed refined waxy distillate

TABLE IV
Harvesting Oils: Mean Treatment Effect On Incidence of Leaf-Burn of Black-Eye Pea (Trial #14/76)

| | Treatments | Period after spraying (Days) | | | | |
|---|---|---|---|---|---|---|
| | | 1 | 3 | 6 | 8 | 14 |
| | | (Phytotoxicity Score)** | | | | |
| 1 | Heavy Gas Oil (RS-1023/76) | 0.5 | 1.8 | 2.2 | 1.3 | 0.8 |
| 2 | DRWD* 20 (RS-1025/76) | 0.7 | 1.6 | 1.4 | 1.3 | 0.8 |
| 3 | DRWD* 5 (RS-1026/76) | 0.8 | 0.8 | 1.0 | 1.3 | 0.3 |
| 4 | Stoddard Solvent (RS-87/76) | 1.2 | 0.8 | 0.3 | 0.8 | 0.2 |
| 5 | EG 9 Gas Oil (RS-1012/76) | 0.6 | 1.0 | 0.3 | 0.3 | 0.0 |
| 6 | Light Cycle Oil (RS-1021/76) | 1.8 | 1.8 | 1.7 | 1.5 | 0.8 |

Rainfall during the trial: 7.58 inches
*Dewaxed refined waxy distillate
**0 = none, 1 = slight, 2 = moderate, 3 = severe

TABLE V
HARVESTING OILS: MEAN TREATMENT EFFECT ON THE INCIDENCE OF LEAF-FALL ON BLACK-EYE PEA (TRIAL NO. 26/76)

| | Treatments | Period after spraying (Days) | | | | | | Total | Rank |
|---|---|---|---|---|---|---|---|---|---|
| | | 5 | 6 | 8 | 12 | 14 | 16 | | |
| | | (Leaf-Fall No.) | | | | | | | |
| 1 | Heavy Gas Oil (RS-1023/76) | 5.7 | 3.0 | 4.0 | 15.3 | 2.3 | 1.7 | 32.0 a* | 1 |
| 2 | Lube Oil Basestock (DRWD** −20 (RS-1025/76) | 7.3 | 1.7 | 1.3 | 4.0 | 4.7 | 3.0 | 22.0 bcde | 5 |
| 3 | Lube Oil Basestock (DRWD** −5 (RS-1026/76) | 2.3 | 1.3 | 3.0 | 11.0 | 5.3 | 2.0 | 25.0 abc | 3 |
| 4 | Stoddard Solvent (RS-87/76) | 3.3 | 1.3 | 0.7 | 8.3 | 5.7 | 4.7 | 24.0 abcd | 4 |
| 5 | EG 9 Gas Oil (RS-1012/76) | 3.7 | 3.3 | 2.0 | 8.7 | 5.3 | 4.0 | 27.0 ab | 2 |
| 6 | Light Cycle Oil (RS-1021/76) | 2.0 | 1.0 | 1.3 | 4.7 | 3.3 | 2.7 | 15.0$^e$ | 6 |
| | S.E. ± | | | | | | | 2.72 | |
| | C.V. % | | | | | | | 21.2 | |

*Figures followed by same letter are not significantly different (5% level)
**Dewaxed refined waxy distillate ex Lube Oil Basestock

TABLE VI

HARVESTING OILS: MEAN TREATMENT EFFECT ON THE INCIDENCE OF LEAF-BURN OF BLACK-EYE PEA (TRIAL NO. 26/76)

| | Treatments | Period after spraying (Days) | | | | | Overall Mean |
|---|---|---|---|---|---|---|---|
| | | 5 | 6 | 8 | 12 | 14 | |
| 1 | Heavy Gas Oil (RS-1023/76) | 2.3 | 2.2 | 2.3 | 2.0 | 1.7 | 2.1 |
| 2 | DRWD* −20 (RS-1025/76) | 1.8 | 2.2 | 2.0 | 1.9 | 1.9 | 2.0 |
| 3 | DRWD* −5 (RS-1026/76) | 2.2 | 2.2 | 2.5 | 1.9 | 2.0 | 2.2 |
| 4 | Stoddard Solvent (RS-87/76) | 1.3 | 1.4 | 0.7 | 0.8 | 0.9 | 1.0 |
| 5 | EG 9 Gas Oil (RS-1021/76) | 0.8 | 1.0 | 2.0 | 1.6 | 1.5 | 1.4 |
| 6 | Light Cycle Oil (RS-1021/76) | 2.2 | 2.2 | 2.0 | 1.8 | 1.7 | 2.0 |

*Dewaxed refined waxy distillate ex Lube Oil Basestock
**0 = none
1 = slight
2 = moderate
3 = severe

TABLE VII

HARVESTING OILS: MEAN TREATMENT EFFECT ON THE INCIDENCE OF LEAF-FALL ON BLACK-EYE PEA (TRIAL #3/77)

| | Treatments | Period after spraying (Days) | | | | | | Total | Rank |
|---|---|---|---|---|---|---|---|---|---|
| | | 1 | 2 | 5 | 7 | 9 | 12 | | |
| 1 | Heavy Gas Oil (RS-1023/76) | 1.3 | 5.7 | 12.7 | 8.7 | 1.0 | 3.0 | 32.3a** | 1 |
| 2 | DRWD*-20 (RS-1025/76) | 2.7 | 2.7 | 8.7 | 3.7 | 1.0 | 1.3 | 20.0abc | 3 |
| 3 | DRWD*-5 (RS-1026/76) | 1.7 | 3.0 | 12.3 | 3.7 | 3.0 | 4.3 | 28.0ab | 2 |
| 4 | Stoddard Solvent (RS-87/76) | 0.0 | 2.3 | 3.0 | 4.7 | 0.0 | 9.0 | 19.0abc | |
| 5 | EG 9 Gas Oil (RS-1012/76) | 1.7 | 0.3 | 8.7 | 6.0 | 2.7 | 3.3 | 22.7abc | 3 |
| 6 | Light Cycle Oil (RS-1021/76) | 3.0 | 2.0 | 3.7 | 5.3 | 2.0 | 2.3 | 18.3abc | |
| | S.E. ± | | | | | | | 4.74 | |
| | C.V. % | | | | | | | 39.7 | |

*Dewaxed refined wax distillate ex Lube Oil Basestock
**Figures followed by same letter not significantly different (5% level)

TABLE VIII

HARVESTING OILS: MEAN TREATMENT EFFECT ON THE INCIDENCE OF LEAF-BURN OF BLACK-EYE PEA (TRAIL #3/77)

| | Treatment | Period after spraying (Days) | | | | | | Overall Mean |
|---|---|---|---|---|---|---|---|---|
| | | 1 | 2 | 5 | 7 | 9 | 12 | |
| 1 | Heavy Gas Oil (RS-1023/76) | 2.3 | 2.3 | 2.6 | 2.8 | 3.0 | 3.0 | 2.6 |
| 2 | DRWD*-20 (RS-1025/76) | 2.2 | 2.2 | 2.5 | 3.0 | 2.7 | 2.7 | 2.5 |
| 3 | DRWD*-5 (RS-1026/76) | 2.2 | 2.2 | 3.0 | 2.7 | 3.0 | 3.0 | 2.6 |
| 4 | Stoddard Solvent (RS-87/76) | 2.8 | 2.8 | 2.7 | 2.7 | 3.0 | 2.5 | 2.7 |
| 5 | EG 9 Gas Oil (RS-1012/76) | 0.6 | 0.6 | 2.7 | 2.8 | 2.7 | 2.8 | 2.0 |
| 6 | Light Cycle Oil (RS-1021/76) | 3.0 | 3.0 | 2.7 | 2.5 | 2.5 | 2.8 | 2.7 |

*Dewaxed refined waxy distillate ex Lube Oil Basestock
**0 = none
1 = slight
2 = moderate
3 = severe

TABLE IX

HARVESTING OILS: OVERALL MEAN TREATMENT EFFECT ON THE INCIDENCE OF LEAF-FALL OF BLACK-EYE PEA (TRIAL NOS. 14/76, 26/76 AND 3/77)

| | Treatments | Overall Mean Total Leaf-fall (No.) | Rank |
|---|---|---|---|
| 1 | Heavy Gas Oil (RS-1023/76) | 35.4 a** | 1 |
| 2 | DRWD*-5 (RS-1026/76) | 28.6 ab | 2 |
| 3 | DRWD*-20 (RS-1025/76) | 26.2 bc | 3 |
| 4 | EG 9 Gas Oil (RS-1012/76) | 25.3 bcd | 4 |
| 5 | Stoddard Solvent (RS-87/76) | 24.0 bcd | 4 |
| 6 | Light Cycle Oil (RS-1021/76) | 16.8 d | 5 |
| | S.E. ± | 2.93 | |
| | C.V. % | 40.0 | |

*Dewaxed refined waxy distillate ex Lube Oil Basestock
**Figures followed by same letter are not significantly different (5% level)

What is claimed is:

1. A process for defoliating and/or desiccating the foliage of leguminous plants which consists essentially in applying to said foliage from 56 to 560 liters per hectare of a composition comprising at least one mineral oil having a viscosity range at 100° F. of between about 34 and 110 SUS, an aromatic content of between 18 and 55 percent; a boiling range of about 180° C. with initial boiling temperatures of between 180° and 420° C.; and a surface tension of between 24 and 28 dines per centimeter at 30° C.; a Harkins Spreading Coefficient for one minute of between 19 and 28 and for 30 minutes of between about 17 and 31 a maximum unsulfonated residue of 85 percent.

2. The process of claim 1 wherein said composition contains also from 0.01 to 1.0 weight/volume percent of a surfactant.

3. The process of claim 2, wherein said surfactant is non-ionic.

4. The process of claim 2, wherein said surfactant is anionic.